(12) United States Patent
Ogino

(10) Patent No.: US 11,344,483 B2
(45) Date of Patent: May 31, 2022

(54) WATER-BASED LIQUID COSMETIC

(71) Applicant: TOKIWA CORPORATION, Nakatsugawa (JP)

(72) Inventor: Kazunori Ogino, Kawaguchi (JP)

( * ) Notice: Subject to any disclaimer, the term of this patent is extended or adjusted under 35 U.S.C. 154(b) by 68 days.

(21) Appl. No.: 16/789,438

(22) Filed: Feb. 13, 2020

(65) Prior Publication Data
US 2020/0261330 A1    Aug. 20, 2020

(30) Foreign Application Priority Data

Feb. 18, 2019 (JP) .............................. JP2019-026388
Mar. 20, 2019 (JP) .............................. JP2019-053207

(51) Int. Cl.
*A61K 8/06* (2006.01)
*A61K 8/88* (2006.01)
*A61K 8/19* (2006.01)
*A61K 8/81* (2006.01)
*A61Q 1/10* (2006.01)

(52) U.S. Cl.
CPC .................. *A61K 8/06* (2013.01); *A61K 8/19* (2013.01); *A61K 8/8129* (2013.01); *A61K 8/8152* (2013.01); *A61K 8/8176* (2013.01); *A61K 8/8182* (2013.01); *A61K 8/88* (2013.01); *A61Q 1/10* (2013.01); *A61K 2800/10* (2013.01); *A61K 2800/43* (2013.01); *A61K 2800/872* (2013.01)

(58) Field of Classification Search
None
See application file for complete search history.

(56) References Cited

U.S. PATENT DOCUMENTS

| | | | |
|---|---|---|---|
| 2005/0002881 A1* | 1/2005 | Aota ........................ | A61K 8/88 424/63 |
| 2009/0087397 A1* | 4/2009 | Travkina ................ | A61K 8/645 424/70.7 |
| 2009/0175813 A1 | 7/2009 | Morita et al. | |
| 2012/0276178 A1* | 11/2012 | Sakuma ............... | A61K 8/8158 424/401 |
| 2018/0369081 A1 | 12/2018 | Sakuma et al. | |
| 2019/0298034 A1* | 10/2019 | Nakamura ........... | A45D 34/042 |

FOREIGN PATENT DOCUMENTS

| | | | |
|---|---|---|---|
| JP | 2005187782 | * | 7/2005 |
| JP | 2007-153744 | | 6/2007 |
| JP | 2016-087094 | | 5/2016 |
| JP | 2017-114825 | | 6/2017 |
| WO | 2007/123115 | | 11/2007 |

OTHER PUBLICATIONS

JP2007153744 Machine Translation, Google Patents, accessed Jun. 25, 2021 (Year: 2021).*
Machine Translation of JP2005187782, Google Patents, accessed Dec. 28, 2021 (Year: 2021).*

* cited by examiner

*Primary Examiner* — Melissa L Fisher
(74) *Attorney, Agent, or Firm* — Soei Patent & Law Firm

(57) ABSTRACT

A water-based liquid cosmetic comprising: sodium polyaspartate; at least one brilliant powder selected from the group consisting of a glass powder coated with a metal or a metal oxide, an aluminum powder, and a resin film powder coated with a metal; a water-soluble dispersant; and at least one metal oxide selected from the group consisting of yellow iron oxide, red iron oxide, black iron oxide, titanium dioxide, titanium oxynitride, and Prussian blue.

13 Claims, 1 Drawing Sheet

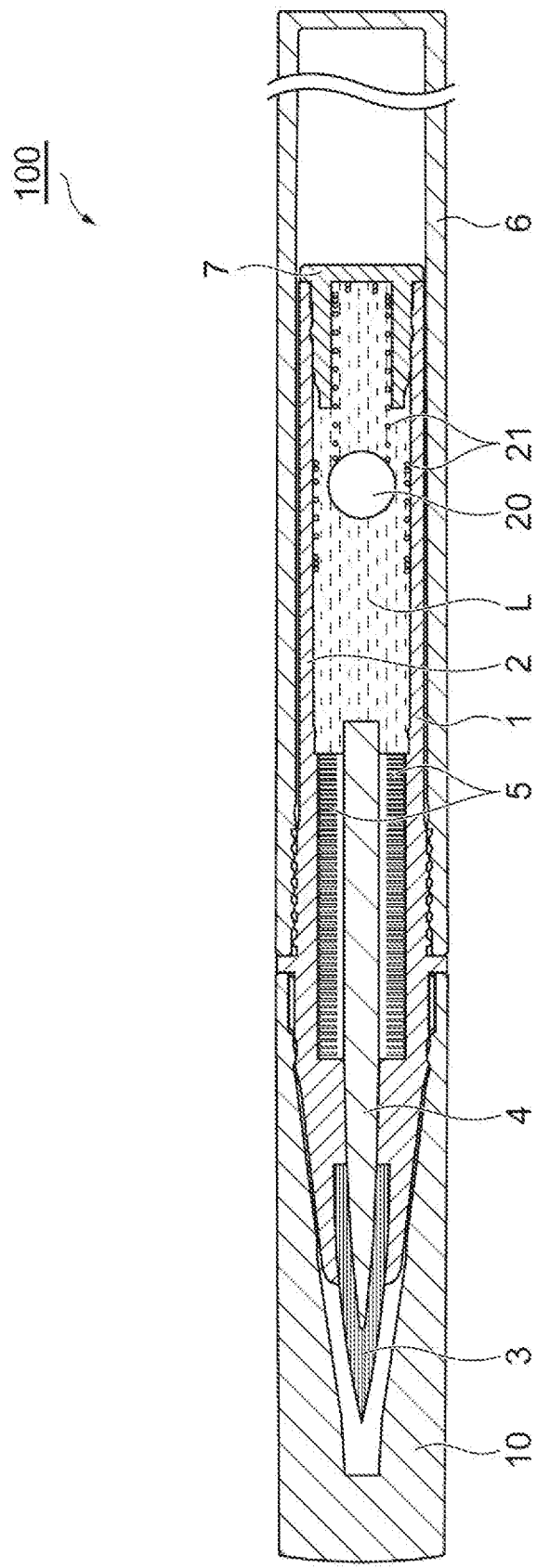

WATER-BASED LIQUID COSMETIC

CROSS-REFERENCE TO RELATED APPLICATIONS

This application claims the benefit of priority from Japanese Patent Application No. 2019-053207, filed on Mar. 20, 2019 and Japanese Patent Application No. 2019-026388, filed on Feb. 18, 2019, the entire contents of which are incorporate herein by reference.

TECHNICAL FIELD

The present application relates to a water-based liquid cosmetic.

BACKGROUND

A pen type cosmetic product and a bottle type cosmetic product are examples of liquid cosmetic products. A bottle type cosmetic product may be obtained by directly filling a container with a cosmetic. A pen type cosmetic product comprises, for example, a cosmetic storing part, such as a fiber bundle impregnated with a cosmetic or a filling part filled with the cosmetic, and an applicator comprising a brush or felt tip joined thereto. Examples thereof include a mechanical type cosmetic product, which forcedly dispenses a liquid cosmetic upon application of force to the storing part through dialing or clicking, and an automatic pen type cosmetic product, which dispenses a liquid cosmetic by the action of its surface tension and capillary phenomenon.

A brilliant powder such as a pearl pigment may be blended in water-based liquid cosmetics, such as eyeliners, in order to achieve a gorgeous and impressive looking eye. Although a brilliant powder can impart pearlescence to a coating layer, the powder is likely to form sediment in the liquid cosmetic because of its particle size which is much larger than those of common coloring pigments. For this reason, when a water-based liquid cosmetic containing a brilliant powder is used in a pen type form with an applicator including an assembly of fine fibers as a brush tip or the like, gaps between the fibers may be clogged with the brilliant powder upon application. When the viscosity of the cosmetic is lowered in order to enhance dispensability and/or enhance the impregnation property of the applicator, the brilliant powder is more likely to form sediment in the cosmetic storing part. When the cosmetic has been left unused for a long period, the sediment made of brilliant powder forms a hard cake and may be insufficiently dispersed in the liquid cosmetic even when stirred. Additionally, the brilliant powder may become stuck in the applicator and/or unable to be moved sufficiently to the applicator. This may result in blur or uneven color tones occurring in lines drawn by the applicator.

Japanese Unexamined Patent Publication No. 2007-153744 discloses a water-based eyeliner composition in which a brilliant pigment, carbon black, a polysaccharide derived from microorganisms, a volatile alcohol, and an alkyl acrylate copolymer emulsion are blended in combination. Japanese Unexamined Patent Publication No. 2017-114825 discloses a liquid cosmetic composition for eye makeup comprising an aqueous emulsion of an acrylic acid-based polymer having a specific Tg, a fermented cellulose, and a flat pigment. Additionally, WO 2007/123115 discloses a water-based liquid makeup cosmetic comprising a flat pigment, a pigment dispersant, a film forming agent, a surfactant in a predetermined amount, and a spherical pigment.

SUMMARY

Known water-based liquid cosmetics comprising a brilliant powder that are used in a pen type form, including those referenced above, do not satisfactorily resolve all the issues of sedimentation and insufficient dispersion of the brilliant powder and the insufficient dispensability of the liquid cosmetic and the pearlescence of the drawn line. For example, cosmetics which include fermented cellulose or polysaccharide derived from microorganisms in an attempt to suppress sedimentation of the brilliant powder may not have satisfactory viscosity.

Disclosed herein is a water-based liquid cosmetic in which a brilliant powder resists the formation of sediment even at a low viscosity, resulting in excellent preservation and stability of the cosmetic. Furthermore, even if the brilliant powder forms sediment, it may be readily dispersed through the liquid cosmetic. Accordingly, the water-based liquid cosmetic can be reliably dispensed from a pen type cosmetic product to form smooth drawn lines having uniform pearlescence.

In some examples, the water-based liquid cosmetic comprises (A) sodium polyaspartate; (B) at least one brilliant powder selected from the group consisting of a glass powder coated with a metal or a metal oxide, an aluminum powder, and a resin film powder coated with a metal, (C) a water-soluble dispersant, and (D) at least one metal oxide selected from the group consisting of yellow iron oxide, red iron oxide, black iron oxide, titanium dioxide, titanium oxynitride, and Prussian blue.

Having the composition described above, the brilliant powder in the water-based liquid cosmetic hardly sediments even at a low viscosity to bring excellent preservation stability of the cosmetic. Even if the brilliant powder once forms sediment, it may be readily dispersed through the liquid cosmetic. The water-based liquid cosmetic may be readily dispensed even from a pen type form product, and may stably form drawn lines having pearlescence.

The water-based liquid cosmetic can be reliably dispensed even if it is in an automatic pen type product. In the automatic pen type products, the capillary force and liquid retention vary depending on the type of applicator that is used. For example, a brush may dispense the cosmetic at a reduced rate as compared to an applicator made of felt. However, the water-based liquid cosmetics disclosed herein can be reliably dispensed even from an automatic pen type product comprising a brush as an applicator.

In order to enhance both viscosity and dispersibility of the brilliant powder and the pigment, the water-soluble dispersant may comprise at least one water-soluble polymer selected from the group consisting of polyvinylpyrrolidone, polyvinyl alcohol, vinylpyrrolidone/vinyl acetate copolymers, and acrylic acid polymers.

In some examples, a content of the sodium polyaspartate may be 0.3 to 5% by mass, a content of the at least one brilliant powder may be 0.5 to 10% by mass, a content of the water-soluble dispersant may be 0.5 to 5% by mass, and a content of the at least one metal oxide may be 0.5 to 10% by mass, based on a total amount of the cosmetic.

In some examples, a content of the sodium polyaspartate may be 10 to 200 parts by mass, a content of the water-soluble dispersant may be 20 to 400 parts by mass, and a content of the at least one metal oxide may be 12.5 to 1000 parts by mass, per 100 parts by mass of the at least one brilliant powder.

In some examples, the at least one brilliant powder may comprise at least one brilliant powder selected from the group consisting of a glass powder coated with a metal or a metal oxide, and an aluminum powder. Additionally, the at least one metal oxide may comprise 12.5 to 1000 parts by mass of at least one metal oxide selected from the group consisting of yellow iron oxide, red iron oxide, black iron oxide, titanium dioxide, and titanium oxynitride, per 100 parts by mass of the total of the glass powder coated with a metal or a metal oxide, and the aluminum powder.

In some examples, the at least one brilliant powder may comprise the resin film powder coated with a metal. Additionally, the at least one metal oxide may comprise 100 to 600 parts by mass of Prussian blue, per 100 parts by mass of the total of the resin film powder coated with a metal.

In order to enhance dispensability, the water-based liquid cosmetic may have a viscosity of 50 mPa·s or less at 25° C.

BRIEF DESCRIPTION OF THE DRAWINGS

FIG. 1 is a schematic cross-sectional view illustrating an example liquid cosmetic container.

DETAILED DESCRIPTION

In the following description, with reference to the drawings, the same reference numbers are assigned to the same components or to similar components having the same function, and overlapping description is omitted.

An example water-based liquid cosmetic comprises (A): sodium polyaspartate (hereinbelow, may be referred to as the "component (A)"), (B): at least one brilliant powder selected from the following group B1 or group B2 (hereinbelow, may be referred to as the "component (B)"), (C): a water-soluble dispersant (hereinbelow, may be referred to as the "component (C)"), and (D): at least one metal oxide selected from the following group D1 or group D2 (hereinbelow, may be referred to as the "component (D)"). Group B1 consists of a glass powder coated with a metal or a metal oxide, and an aluminum powder, and group B2 consists of a resin film powder coated with a metal. Group D1 consists of yellow iron oxide, red iron oxide, black iron oxide, titanium dioxide, and titanium oxynitride, and group D2 consists of Prussian blue.

In one or more embodiments, the term "water-based" may be understood to mean that at least water is contained in the water-based liquid cosmetic. The water-based cosmetic may further comprise a lower alcohol having 1 to 5 carbon atoms, such as ethanol, in addition to water.

In one or more embodiments, a content of water in the water-based liquid cosmetic may be 30 to 90% by mass, may be 40 to 80% by mass, or may be 50 to 70% by mass, based on a total amount of the cosmetic.

In one or more embodiments, the term "liquid" may be understood to refer to a substance, such as a cosmetic product, having fluidity at 25° C. A viscosity at 25° C. of the water-based liquid cosmetic may be 10,000 mPa·s or less at 25° C. and may be appropriately set, depending on the form of a container. For example, in the case of a bottle type container, a cosmetic having a viscosity of 10,000 mPa·s or less at 25° C. may be used, while in the case of a pen type container, a cosmetic having a viscosity of 5000 mPa·s or less at 25° C. may be used.

In order to enhance dispensability in an automatic pen type product, the water-based liquid cosmetic may have a viscosity of 50 mPa·s or less, 40 mPa·s or less, 35 mPa·s or less, 30 mPa·s or less, 25 mPa·s or less, or 20 mPa·s or less at 25° C. In some examples, the dispensability may be further improved by employing the cosmetic with a viscosity in one of the increasingly lower ranges disclosed above, such as "20 mPa·s or less." In order to enhance usability, the water-based liquid cosmetic may have a viscosity of 4 mPa·s or more, or 6 mPa·s or more at 25° C. The usability may be further improved by employing the cosmetic with a viscosity in the higher range disclosed above, such as "6 mPa·s or more."

The viscosity described above refers to a measured value of a sample at 25° C. using a Brookfield type viscometer (BM type) under the following conditions.

5 to 50 mPa·s: BL adapter with a rotational speed of 12 rpm 50 to 500 mPa·s: Rotor No. 1 with a rotational speed of 12 rpm 250 to 2500 mPa·s: Rotor No. 2 with a rotational speed of 12 rpm 1,000 to 10,000 mPa·s: Rotor No. 3 with a rotational speed of 12 rpm 5,000 to 50,000 mPa·s: Rotor No. 4 with a rotational speed of 12 rpm (A) Sodium Polyaspartate Examples of the sodium polyaspartate include sodium salts of aspartic acid polymers that are used for cosmetics, as well as other products such as AQUADEW SPA-30B (trade name, manufactured by Ajinomoto Co., Inc., with a solid content of 30% by mass).

In one or more embodiments, a content of the sodium polyaspartate in the water-based liquid cosmetic may be 0.3 to 5% by mass, 0.4 to 4% by mass, 0.5 to 3% by mass, or 0.5 to 2% by mass, based on a total amount of the cosmetic. In some examples, the ability to ensure that the brilliant powder remains uniformly dispersed throughout the cosmetic product, even in the case of occasional or transitional sedimentation, may be improved by employing the content of the sodium polyaspartate in one of the increasingly narrower ranges disclosed above, such as "0.5 to 2% by mass."

Component (B)

In some examples, at least one brilliant powder selected from group B1 and group B2 may be used as the component (B). Group B1 consists of a glass powder coated with a metal or a metal oxide, and an aluminum powder, and group B2 consists of a resin film powder coated with a metal.

Examples of the glass powder coated with a metal or a metal oxide include a titanium oxide-coated glass powder, an iron oxide-coated glass powder, a silver-coated glass powder, and a gold-coated glass powder.

Examples of the resin film powder coated with a metal include a polyethylene terephthalate-aluminum-epoxy laminate powder, a polyethylene terephthalate-silver-epoxy laminate powder, and a polyethylene terephthalate-aluminum laminate powder.

In some examples, characteristics such as the ability to readily dispense the cosmetic and to maintain a uniform dispersion of the brilliant powder, may be enhanced by including aluminum powder in the cosmetic product.

Whereas the example ingredients of the brilliant powder described above may be used alone as the component (B), in some examples two or more powders may be used in combination as component (B) in order to vary the characteristics of the cosmetic.

The brilliant powder may have a specific gravity of 4.5 g/cm$^3$ or less, 1.5 to 3.5 g/cm$^3$, or 2 to 3 g/cm$^3$, in order to suppress sedimentation. In some examples, the sedimentation may be further suppressed by employing the brilliant powder with the specific gravity in one of the increasingly narrower ranges disclosed above, such as "2 to 3 g/cm$^3$".

In one or more embodiments, the term "specific gravity" may be understood to mean a true specific gravity. For example, a powder having a true specific gravity as described below, may be used as the brilliant powder.

Aluminum powder: 2.4 to 2.7

Glass powder coated with a metal or a metal oxide: 2.5 to 3.5

Resin film powder coated with a metal: 1.3 to 1.6

In some examples, the brilliant powder may have an average particle size of 1 to 50 μm, 5 to 40 μm, or 8 to 30 μm. In some examples, the ability to obtain a cosmetic having excellent pearlescence and dispensability may be enhanced by including one of the increasingly narrower ranges of average particle size disclosed above, such as "8 to 30 μm."

In one or more of embodiments, a content of the brilliant powder in the water-based liquid cosmetic may be 0.5 to 10% by mass, 0.6 to 9% by mass, 0.7 to 8% by mass, or 0.8 to 7% by mass, based on a total amount of the cosmetic. In some examples, the ability to further improve the pearlescence and dispensability of the cosmetic may be enhanced by including one of the increasingly narrower ranges of content disclosed above, such as "0.8 to 7% by mass."

(C) Water-Soluble Dispersant

Examples of the water-soluble dispersant include a water-soluble polymer such as polyvinylpyrrolidone (PVP), polyvinyl alcohol (PVA), vinylpyrrolidone/vinyl acetate copolymers (VP/VA copolymers), and acrylic acid polymers. Examples of the acrylic acid polymer include acrylic acid-alkyl acrylate ester copolymers. The acrylic acid and alkyl acrylate herein respectively include methacrylic acid and alkyl methacrylate. The water-soluble polymers described above may be compounded in the water-based liquid cosmetic in a faun of a mixed solution with water, ethanol, a polyhydric alcohol, or a mixture of the foregoing.

The water-soluble polymer may employ a commercially available product, including PVP K-30, 60, and 90 series (trade name, manufactured by ISP Japan Ltd.), PVP/VA S-630 and PVP/VA W-735 (trade name, manufactured by ISP Japan Ltd.), KURARAY POVAL PVA series (manufactured by KURARAY CO., LTD.), and Luvimer 100P (trade name, manufactured by BASF SE).

These water-soluble dispersants may be used alone, or two or more thereof may be used in combination.

In one or more embodiments, the water-based liquid cosmetic may comprise at least one water-soluble polymer selected from the group consisting of polyvinylpyrrolidone, polyvinyl alcohol, vinylpyrrolidone/vinyl acetate copolymers, and acrylic acid polymers, in order to enhance both the adjustability of the viscosity of the cosmetic and the dispersibility of the brilliant powder and pigment.

In one or more embodiments, a content of the component (C) in the water-based liquid cosmetic may be 0.5 to 5% by mass, 0.6 to 4.5% by mass, 0.7 to 4% by mass, or 0.8 to 3.5% by mass, based on a total amount of the cosmetic. In some examples, the ability to further improve the dispersibility and dispensability of the cosmetic may be enhanced by including one of the increasingly narrower ranges of content disclosed above, such as "0.8 to 3.5% by mass."

Component (D)

The component (D) may be blended in order to impart coloring and suppress sedimentation of the brilliant powder. In some examples, at least one metal oxide selected from group D1 and group D2 may be used as the component (D). Group D1 consists of yellow iron oxide, red iron oxide, black iron oxide, titanium dioxide, titanium oxynitride (titanium black), and group D2 consists of Prussian blue.

The component (D) may employ those surface-treated by using a silicone compound, a fluorine compound, metal soap, collagen, a hydrocarbon, a higher fatty acid, lecithin, a higher alcohol, ester, wax, a surfactant, or others. In order to further improve the dispersibility of the brilliant powder, the component (D) may be used in the form of a dispersion including water as solvent.

Whereas the example ingredients described above may be used alone as the component (D), in other examples two or more of the ingredients may be used in combination as component (D) in order to vary the characteristics of the cosmetic.

The metal oxide may have an average particle size of 0.5 μm or less, 0.1 to 0.4 μm, or 0.15 to 0.35 μm and, in some examples, the dispensability of the cosmetic from a container may be enhanced by including one of the increasingly narrower ranges of particle size disclosed above, such as "0.15 to 0.35 μm."

Additionally, the metal oxide may have a specific gravity of 3 g/cm$^3$ or more, 3 to 6 g/cm$^3$, or 3 to 5 g/cm$^3$.

In some examples, the cosmetic product may comprise one or more metal oxides having a true specific gravity as provided below.

Yellow iron oxide: 3.4 to 4.1

Red iron oxide: 4.2 to 5.2

Black iron oxide: 4.5 to 5.5

Titanium oxide: 3.5 to 4.2

Titanium oxynitride (titanium black): 4.3

Prussian blue: 1.7 to 1.9

In one or more embodiments, a content of the component (D) in the water-based liquid cosmetic may be 0.5 to 10% by mass, 1 to 9% by mass, 2 to 8% by mass, or 3 to 7% by mass, based on a total amount of the cosmetic. In some examples, both clogging of the brilliant powder in the container and blur of drawn lines may be reduced, while the pearlescence of the cosmetic product sufficient for drawn lines may be enhanced, by including one of the increasingly narrower ranges of content disclosed above, such as "3 to 7% by mass."

In one or more embodiments, a content of the component (A) in the water-based liquid cosmetic may be 10 to 200 parts by mass per 100 parts by mass of the component (B). To help ensure that the brilliant powder remains uniformly dispersed throughout the cosmetic product, even in the case of occasional or transitional sedimentation of the brilliant powder, a content of the component (A) in the water-based liquid cosmetic may be 15 to 180 parts by mass or 20 to 160 parts by mass, per 100 parts by mass of the component (B).

In one or more embodiments, a content of the component (C) in the water-based liquid cosmetic may be 20 to 1000 parts by mass per 100 parts by mass of the component (B). In order to enhance both the adjustability of the viscosity of the cosmetic product and the dispersibility of the brilliant powder and the pigment, a content of the component (C) in the water-based liquid cosmetic may be 20 to 500 parts by mass, 20 to 400 parts by mass, 35 to 500 parts by mass, or 45 to 400 parts by mass, per 100 parts by mass of the component (B). In some examples, certain characteristics of the cosmetic product such as adjustability of viscosity and dispersibility may be enhanced by including one of the increasingly narrower ranges of contents disclosed above, such as "45 to 400 parts by mass."

A content ratio between the component (A) and the component (C), specifically a mass ratio component (A)/component (C), may be 0.06 to 10, and from the viewpoint of suppression of sedimentation of the brilliant powder, and enhancing both uniform dispersibility of the brilliant powder even in the case of occasional or transitional sedimentation and dispensability of the cosmetic product from a container, it may be 0.1 to 5 or 0.15 to 2.

In one or more embodiments, a content of the component (D) in the water-based liquid cosmetic may be 12.5 to 1500 parts by mass or 12.5 to 1000 parts by mass per 100 parts by mass of the component (B). From the viewpoint of suppressing sedimentation and improving uniform dispersibility of the brilliant powder even in the case of occasional or transitional sedimentation while enhancing the pearlescence of drawn lines, a content of the component (D) in the water-based liquid cosmetic may be 15 to 1200 parts by mass or 30 to 1000 parts by mass, per 100 parts by mass of the component (B).

In some examples, the component (B) comprises at least one brilliant powder selected from group B1 (hereinbelow, may be referred to as the "component (B1)"), and the component (D) may comprise at least one metal oxide selected from group D1 (hereinbelow, may be referred to as the "component (D1)"). A content of component (D1) may comprise an amount of 10 to 1000 parts by mass, 12.5 to 1000 parts by mass or 20 to 900 parts by mass, per 100 parts by mass of the total of the components (B1), in order to enhance the uniform dispersibility of the brilliant powder even in the case of occasional or transitional sedimentation while suppressing sedimentation and clogging of the brilliant powder in a container and reducing the blur of drawn lines.

In some examples, the component (B) comprises the component (B1), and the component D may comprise a combination of a metal oxide selected from group D2 (hereinbelow, may be referred to as the "component (D2)") and the component (D1). In other examples, the component (D) may only comprise the component (D2).

When the component (D1) and the component (D2) are used in combination, a total content of these components may be 10 to 1000 parts by mass, 20 to 900 parts by mass, or 30 to 800 parts by mass, per 100 parts by mass of the component (B1). When the component (D1) and the component (D2) are used in combination, a content ratio between the component (D1) and the component (D2), specifically a mass ratio component (D1)/component (D2), may be 0.01 to 100 or 0.03 to 6.5.

When only the component (D2) is used as the component (D), a content of the component (D2) may be 10 to 1000 parts by mass, 20 to 900 parts by mass, or 30 to 800 parts by mass, per 100 parts by mass of the component (B1).

In some examples, the component (B) comprises a brilliant powder selected from group B2 (hereinbelow, may be referred to as the "component (B2)"), and the component (D) may comprise a metal oxide selected from group D2 (hereinbelow, may be referred to as the "component (D2)"). The content of component (D2) may be an amount of 10 to 1000 parts by mass, 20 to 900 parts by mass or 100 to 600 parts by mass, per 100 parts by mass of a total of the component (B2), in order to enhance the uniform dispersibility of the brilliant powder even in the case of occasional or transitional sedimentation, while suppressing sedimentation and clogging of the brilliant powder in a container and reducing the blur of drawn lines.

In some examples, the component (B) comprises the component (B2), and the component (D) may comprise a combination of the component (D1) and the component (D2). In other examples, the component (D) may only comprise the component (D2).

When the component (D1) and the component (D2) are used in combination, a total content of these components may be 10 to 1000 parts by mass, 20 to 900 parts by mass, or 30 to 800 parts by mass, per 100 parts by mass of the component (B2). A content ratio between the component (D1) and the component (D2), specifically a mass ratio component (D1)/component (D2), may be 0.1/10 to 10/0.1, or 0.3/10 to 10/1.5.

In some examples, the component (B1) or the component (B2) may be used exclusively as the component (B). In other examples, the component (B1) and the component (B2) may be used in combination as the component (B). When the component (B1) and the component (B2) are used in combination, a content ratio between the component (B1) and the component (B2), specifically a mass ratio component (B1)/component (B2), may be 0.01 to 20, or 0.1 to 18.

In one or more embodiments, a total content of the component (B) and the component (D) in the water-based liquid cosmetic may be 0.5% by mass to 20% by mass, 0.6% by mass to 18% by mass, or 0.7% by mass to 15% by mass, based on a total amount of the cosmetic. In some examples, sedimentation may be suppressed and both the uniform dispersibility of the brilliant powder even in the case of occasional or transitional sedimentation and the pearlescence of drawn lines may be enhanced by selecting a total content of the component (B) and the component (D) in one of the increasingly narrower ranges, such as "0.7% by mass to 15% by mass."

In still other examples, the water-based liquid cosmetic may comprise a powder other than the component (B) or the component (D) (hereinbelow, may be referred to as "other powder").

Examples of the other powder include: colored inorganic pigments, such as carbon black, chromium hydroxide, ultramarine, and titanium nitride; white inorganic pigments, such as barium sulfate; organic pigment powders, such as Red No. 201, Red No. 202, Red No. 205, Red No. 226, Red No. 228, Orange No. 203, Orange No. 204, Blue No. 404, and Yellow No. 401; organic pigment powders including zirconium, barium or aluminum lakes, such as Red No. 3, Red No. 104, Red No. 106, Orange No. 205, Yellow No. 4, Yellow No. 5, Green No. 3, and Blue No. 1; white extender powders, such as talc, muscovite, phlogopite, lepidolite, biotite, synthesized mica, sericite, synthesized sericite, kaolin, silicon carbide, bentonite, smectite, diatomaceous earth, aluminum silicate, magnesium aluminum metasilicate, calcium silicate, barium silicate, magnesium silicate, calcium carbonate, magnesium carbonate, hydroxyapatite, and boron nitride; synthesized resin powders, such as polyamide-based resins, polyethylene-based resins, polyacrylic-based resins, polyester-based resins, fluorine-based resins, cellulose-based resins, polystyrene-based resins, and styrene-acryl copolymer resins; organic polymer resin powders, such as polypropylene-based resins and urethane resins; organic low-molecular powders, such as zinc stearate and N-acyllysine; natural organic powders, such as silk powder and cellulose powder; and brilliant powders other than the component (B), such as titanated mica, pigment-coated titanated mica, silver powder, fish scale foil, and bismuth oxychloride.

The other powders may be used alone, or two or more thereof may be used in combination.

Among the other powders described above, carbon black may be selected to enhance certain characteristics of the cosmetic product such as depth and the effect of highlighting pearlescence of drawn lines.

In some examples, the water-based liquid cosmetic may comprise a film-forming polymer emulsion, from the viewpoint of preventing secondary adhesion of cosmetic films, imparting water resistance to the cosmetic films, and facilitating makeup removal.

Examples of a polymer contained in the film-forming polymer emulsion include water-insoluble polymers or copolymers containing alkyl (meth)acrylate monomers as constituent units. Examples of the constituent units of the copolymer include a vinyl acetate monomer and a styrene monomer. The copolymer may be a random copolymer, a graft copolymer, a block copolymer, or a core-shell-type copolymer.

Examples of the film-forming polymer emulsion include alkyl acrylate copolymer emulsions, alkyl acrylate-styrene copolymer emulsions, and alkyl acrylate-vinyl acetate copolymer emulsion. The alkyl acrylate referred to herein includes an alkyl methacrylate. In one or more embodiments, the film-forming polymer emulsion may comprise water as the medium and have a solid content of 30 to 60% by mass.

The film-forming polymer emulsion may employ a commercial product. Examples of the alkyl acrylate copolymer emulsion include YODOSOL GH800F (trade name, manufactured by Akzo Nobel Company, with a solid content of 45% by mass), YODOSOL GH810F (trade name, manufactured by Akzo Nobel Company, with a solid content of 46% by mass), YODOSOL GH34F (trade name, manufactured by Akzo Nobel Company, with a solid content of 42% by mass), and DAITOSOL 5000SJ (trade name, manufactured by Daito Kasei Kogyo Co., Ltd., with a solid content of 50% by mass). Examples of the alkyl acrylate-styrene copolymer emulsion include YODOSOL GH41F (trade name, manufactured by Akzo Nobel Company, with a solid content of 45% by mass), DAITOSOL 5000STY (trade name, manufactured by Daito Kasei Kogyo Co., Ltd., with a solid content of 50% by mass), and EMUPOLY CE-119N (trade name, sold by Nikko Chemicals Co., Ltd.). Examples of the alkyl acrylate-vinyl acetate copolymer emulsion include VINYSOL 2140L (trade name, manufactured by Daido Chemical Corporation, with a solid content of 45% by mass).

The film-forming polymer emulsion may be used alone, or two or more thereof may be used in combination.

In one or more embodiments, a content of the film-forming polymer emulsion in the water-based liquid cosmetic may be 5 to 20% by mass, 6 to 15% by mass, or 7 to 12% by mass as a solid content, based on a total amount of the cosmetic. In some examples, the ability to facilitate makeup removal while preventing secondary adhesion and enhancing the water resistance of cosmetic films may be improved by selecting a content of the film-forming polymer emulsion in one of the increasingly narrower ranges, such as "7 to 12% by mass."

In one or more embodiments, the water-based liquid cosmetics may comprise, in addition to the components described above, other components that may be used to impart one or more additional characteristics in the cosmetics. For example, any one or more of a surfactant, a moisturizing agent, a viscosity modifier, a preservative, a pH adjusting agent, a chelator, an ultraviolet absorber, a vitamin, a beauty ingredient, an antioxidant, and a fragrance may be added in such a range that does not impair the previously described effects of the disclosed cosmetics.

Examples of the surfactant that may be used include hydrophilic nonionic surfactants, anionic surfactants other than sodium polyaspartate, cationic surfactants, and amphoteric surfactants.

Examples of the hydrophilic nonionic surfactant include polyoxyalkylene alkyl ethers, glycerin alkyl ethers, glycerin fatty acid esters, polyglycerin fatty acid esters, sorbitan fatty acid esters, and alkylene glycol adducts thereof, polyalkylene glycol fatty acid esters, polyglycerin-modified silicones, and polyether-modified silicones. Examples of the anionic surfactant include alkyl phosphate ester salts, polyoxyalkylene alkyl ether phosphate salts, sulphonate salts, alkyl sulfate salts, and polyaspartate salts other than sodium polyaspartate salt. Examples of the cationic surfactant include alkylamine salts and alkyltrimethyl ammonium salts. Examples of the amphoteric surfactant include lecithin, carbobetaine type amphoteric surfactants, sulfobetaine type amphoteric surfactants, and amino acid type amphoteric surfactants.

Examples of the viscosity modifier include clay mineral and polysaccharides. In some examples, synthesized smectite may be used to facilitate the ease of uniform dispersibility.

In one or more embodiments, the water-based liquid cosmetic may be produced by dissolving or dispersing the component (A), the component (B), the component (C), and the component (D) described above, with water and/or other components, and by stirring and mixing the mixture uniformly.

The water-based liquid cosmetic may be used as a makeup cosmetic, such as an eyeliner, an eyebrow cosmetics, an eyeshadow, or a mascara. The excellent pearlescence of drawn lines, for example, makes the cosmetic useful as eyeliners.

In one or more embodiments, the water-based liquid cosmetic may be utilized in a cosmetic product. Examples products include a pen type product and a bottle type product. The pen type product may comprises a cosmetic storing part, such as a fiber bundle impregnated with a liquid cosmetic or a part filled with a liquid cosmetic, and an applicator comprising a brush or felt tip joined thereto. Examples of the pen type cosmetic product include a mechanical type product, which forcedly dispenses the cosmetic upon application of force on the storing part by dialing or clicking, and an automatic pen type product, which dispenses the cosmetic by the action of its surface tension and capillary phenomenon.

From the viewpoint of convenience in use and portability, the water-based liquid cosmetic may be utilized in an automatic pen type product. The automatic pen type product may employ a container, such as the liquid cosmetic container disclosed in Japanese Unexamined Patent Publication No. 2016-87094.

FIG. 1 is a schematic cross-sectional view showing an example liquid cosmetic container 100. The overall shape of the liquid cosmetic container 100 resembles a writing tool in an elongated narrow round-bar form. In some examples, the container 100 comprises a cylindrical container body 1, a storing part 2 disposed in the container body 1 so as to accommodate a water-based liquid cosmetic L, and a brush 3 installed at a tip of the container body 1 for the application of the water-based liquid cosmetic L in the storing part 2. Additionally, the container 100 may comprise a shaft-like relay wick 4 disposed in the container body 1 for connecting the inner part of the storing part 2 to the brush 3, and a bellows component 5 in a substantially cylindrical shape installed around the relay wick 4. In some examples, a grip tube 6 in a bottomed-cylindrical shape is screwed to the container body 1 for detachable installation so that a user holding the container body 1 can easily apply the cosmetic. The shape of the container body 1 may be cylindrical, rectangular tube, or some other shape.

The container body 1 is formed of PP (i.e., polypropylene), for example, and is configured to be a tapered cylindrical shape having a flange. A rear end face of the flange part disposed on an outer peripheral surface of the container body 1 abuts on a front end face of the gripping cylinder 6 screwed into the container body 1. A front end face of the flange part abuts on an open end face of a cap 10 installed on the container body 1. An opening at a rear end of the container body 1 is closed with a bottomed cylindrical tale plug 7 inserted therein.

A bellows component 5 is configured to control the flow of the water-based liquid cosmetic L and has a groove (bellows) containing the water-based liquid cosmetic L. A cylindrical rear end part of the bellows component 5 fits in a recess of an inner peripheral face of the container body 1 so that the bellows component 5 is installed within the container body 1. The storing part 2 is formed between the rear end part of bellows component 5 in the container body 1 and the tail plug 7, and the water-based liquid cosmetic L is accommodated in this storing part 2.

The relay wick 4 is, for example, foil led of an acrylic resin and extends in the axial direction so as to pass through the tube hole of the bellows component 5. A tip of the relay wick 4 fits into a tip of the bellows component 5 so that the relay wick 4 is installed within the bellows component 5. The relay wick 4 connects the inner part of the storing part 2 to the brush 3, while its rear end part enters into the inner part of the storing part 2 and its front end part enters into the brush 3. The relay wick 4 allows the water-based liquid cosmetic L to be sucked from the storing part 2 by capillary phenomenon and to be supplied to the brush 3.

The brush serves as an applicator in the liquid cosmetic container 100 shown in FIG. 1 but it may be replaced by a felt tip or an urethane tip.

The bottomed-cylindrical cap 10 is detachably installed at the tip of the container body 1 by fitting to protect the brush 3.

The storing part 2 of the liquid cosmetic container 100 accommodates a stirring element 20 that is movable in the axial direction and a coil spring 21 that is extendable in the axial direction, together with the water-based liquid cosmetic L. In FIG. 1, the stirring element 20 is depicted as a sphere; however, the element may be a polyhedron, a cone or other shape depending on the particular application.

A coil spring 21 is an integrally-formed spring including a plurality of spring parts having different diameters (e.g., two spring parts having different diameters as illustrated in FIG. 1) integrally connected in the axial direction, which may be formed of SUS (Steel Use Stainless), for example. This coil spring 21 comprises a small-diameter spring part having a diameter smaller than that of the stirring element 20 in its rear half part and a large-diameter spring part having a diameter larger than that of the stirring element 20 continuously, the latter of which spring parts is adjacent to the forward axial direction of the small-diameter spring.

When a user shakes the container 100, the stirring element 20 that is movable in the axial direction in the large-diameter spring of the coil spring 21 moves in the axial direction. Thus, the water-based liquid cosmetic L is stirred by the movement of the stirring element 20.

In the liquid cosmetic container 100 thus configured, the water-based liquid cosmetic L in the storing part 2 flows toward the brush 3 at a front side of the container through the rely wick 4, whereby it is provided to a user for application with the brush 3. The liquid cosmetic container 100 includes the stirring element 10 and the coil spring 21, thereby allowing the water-based liquid cosmetic L to efficiently flow toward the brush 3. This configuration may be changed such that it neither includes the stirring element 10 nor the coil spring 21.

An example automatic pen type container that may utilize the water-based liquid cosmetic has been described above by referring to the liquid cosmetic container 100 having a so-called direct liquid type structure. However, other types of structures may be used. For example, a container having a so-called wadding structure may be used, which omits the bellows components 5, the stirring element 20 and the coil spring 21 in the liquid cosmetic container 100 and which has a storing part 2 accommodating a wadding component impregnated with the water-based liquid cosmetic L and sucks the water-based liquid cosmetic L therefrom to supply to the brush 3 through a rear end part of the relay wick 4 entering into an inner part of the wadding component.

ADDITIONAL EXAMPLE EMBODIMENTS

Hereinafter, details of additional example embodiments will be described with reference to comparative examples.

Production of Water-Based Liquid Cosmetics

Examples 1 to 29 and Comparative Examples 1 to 3

The respective ingredients listed in Tables 1 to 6 were mixed at the ratios (% by mass) shown in the corresponding tables with a disperser to obtain each of the water-based liquid cosmetics. Each of the values of polymer emulsions in the tables is the amount of an emulsion to be compounded. Each of the values of aminomethyl propanol represents the amount of a 50% aqueous solution of aminomethyl propanol to be compounded.

The respective ingredients shown in Tables 1 to 6 employed those described below.

Brilliant powder*1: polyethylene terephthalate-aluminum-epoxy laminate powder, manufactured by KAKU-HACHI CO., LTD., trade name "Alumiflake silver 0.15 mm"

Alkyl acrylate copolymer*1: acrylates copolymer, manufactured by BASF SE, trade name "Luvimer 100P"

Polymer emulsion-1: alkyl acrylate copolymer emulsion, manufactured by Daito Kasei Kogyo Co., Ltd., trade name "DAITOSOL 5000SJ", with a solid content of 50% by mass Polymer emulsion-2: alkyl acrylate-styrene copolymer emulsion, manufactured by Akzo Nobel Company, trade name "YODOSOL GH41F" with a solid content of 45% by mass Polymer emulsion-3: manufactured by Daito Kasei Kogyo Co., Ltd., trade name "VINYSOL 2140L" with a solid content of 47.5% by mass Viscosity of Water-Based Liquid Cosmetics The viscosity of a sample was measured at 25° C. using a Brookfield-type viscometer (BM type) under the following conditions.

The measurement time was set at one minute.

5 to 50 mPa·s: BL adapter with a rotational speed of 12 rpm 50 to 500 mPa·s: rotor No. 1 with a rotational speed of 12 rpm 250 to 2500 mPa·s: rotor No. 2 with a rotational speed of 12 rpm 1000 to 10000 mPa·s: rotor No. 3 with a rotational speed of 12 rpm 5000 to 50000 mPa·s: rotor No. 4 with a rotational speed of 12 rpm Evaluation I of Water-Based Liquid Cosmetic Dispersibility of Brilliant Powder (Degree of Sedimentation)

Each sample of the water-based liquid cosmetics was placed in a glass tube and left under a 25° C. environment for one day. The sedimentation level of the brilliant powder in the tube was visually observed, and the dispersibility of the brilliant powder (degree of sedimentation) was evaluated according to the following evaluation criteria.

(Evaluation Criteria)

A: The brilliant powder can be visually observed in the whole liquid.

B: The brilliant powder can be visually observed from the bottom to the intermediate part of the liquid.

C: The brilliant powder can be visually observed from the bottom to the lower part of the liquid.

D: The brilliant powder can be visually observed only in the bottom of the liquid.

Redispersibility of Brilliant Powder

After each sample of the water-based liquid cosmetics was placed in a glass tube and left under a 25° C. environment for a week, the glass tube was shaken by hand for 10 seconds, and the redispersibility of the brilliant powder (dispersibility of the brilliant powder after the powder once forms sediments) was visually observed. The redispersibility of the brilliant powder was evaluated according to the following evaluation criteria.

A: Immediately after shaking, all the lumps of the brilliant powder at the bottom of the tube become loose, and the brilliant powder can be visually observed in the whole liquid.

B: After 10 seconds of shaking, all the lumps of the brilliant powder at the bottom of the tube become loose, and the brilliant powder can be visually observed in the whole liquid.

C: A few of the lumps of the brilliant powder at the bottom of the tube become loose, but the lumps do not completely disappear.

D: There is no change after shaking, and the lumps of the brilliant powder at the bottom of the tube do not become loose.

Evaluation II of Water-Based Liquid Cosmetics

The water-based liquid cosmetic obtained above was filled in an storing part of a liquid eyeliner container of an automatic pen type having the same structure as that of the container shown in FIG. 1 (applicator: brush, relay wick: acryl resin) to produce a filled product.

The filled product (immediately after filling and after a preservation test (left under a 25° C. environment for a week)) was evaluated with respect to its pearlescence and dispensability by the following evaluation methods.

Evaluation of Pearlescence

Three lines having a width of 2 mm and a length of 4 cm were drawn with the filled product on the back of a hand. The pearlescence of the drawn lines was visually observed, and the pearlescence was evaluated according to the following evaluation criteria.

(Evaluation Criteria)

A: Pearlescence equivalent to that of the liquid before filling can be visually observed.

B: Pearlescence that is slightly inferior to that of the liquid before filling but is sufficient can be visually observed.

C: Pearlescence is considerably inferior to that of the liquid before filling.

D: No pearlescence is substantially present compared to the liquid before filling.

Evaluation of Dispensability

Three lines having a width of 2 mm and a length of 4 cm were drawn with the filled product on the back of a hand. The dispensability of the cosmetic on drawing was visually observed, and the dispensability was evaluated according to the following evaluation criteria.

(Evaluation Criteria)

A: The amount of the liquid dispensed is sufficient, and the drawn lines are uniform.

B: The amount of the liquid dispensed has no problem, and the drawn lines are substantially uniform.

C: The amount of the liquid dispensed is relatively small, and the drawn lines are slightly uneven.

D: The amount of the liquid dispensed is small, and the drawn lines blur.

TABLE 1

| | | | Example | | | | | |
|---|---|---|---|---|---|---|---|---|
| | | | 1 | 2 | 3 | 4 | 5 | 6 |
| 1 | (A) | Na polyaspartate | 1.00 | 1.00 | 1.00 | 1.00 | 1.00 | 1.00 |
| 2 | | Synthesized smectite | 0.10 | 0.10 | 0.10 | 0.10 | 0.10 | 0.10 |
| 3 | (B) | Aluminum powder | 4.00 | 4.00 | 4.00 | 4.00 | 4.00 | 4.00 |
| 4 | | Titanium oxide-coated glass powder | — | — | — | — | — | — |
| 5 | | Brilliant powder*1 | — | — | — | — | — | — |
| 6 | (C) | PVP | 2.00 | 2.00 | 2.00 | 2.00 | 2.00 | 2.00 |
| 7 | | PVA | — | — | — | — | — | — |
| 8 | | VP/VA copolymer | — | — | — | — | — | — |
| 9 | | Alkyl acrylate copolymer*1 | — | — | — | — | — | — |
| 10 | (D) | Red iron oxide | 5.00 | 5.00 | 2.00 | 1.00 | 0.50 | 9.00 |
| 11 | | Black iron oxide | — | — | — | — | — | — |
| 12 | | Yellow iron oxide | — | — | — | — | — | — |
| 13 | | Titanium dioxide | — | — | — | — | — | — |
| 14 | | Titanium black | — | — | — | — | — | — |
| 15 | | Prussian blue | — | — | — | — | — | — |
| 16 | | Carbon black | 3.50 | — | 3.50 | 3.50 | 3.50 | 3.50 |
| 17 | | Polymer emulsion-1 | 10.00 | 10.00 | 10.00 | 10.00 | 10.00 | 10.00 |

TABLE 1-continued

| | | | Example | | | | | |
|---|---|---|---|---|---|---|---|---|
| | | | 1 | 2 | 3 | 4 | 5 | 6 |
| 18 | | Polymer emulsion-2 | — | — | — | — | — | — |
| 19 | | Polymer emulsion-3 | — | — | — | — | — | — |
| 20 | | Polyoxyethylene alkyl ether | 1.00 | 1.00 | 1.00 | 1.00 | 1.00 | 1.00 |
| 21 | | Polyoxyethylene glycerin fatty acid ester | 1.00 | 1.00 | 1.00 | 1.00 | 1.00 | 1.00 |
| 22 | | Aminomethyl propanol | 0.10 | 0.10 | 0.10 | 0.10 | 0.10 | 0.10 |
| 23 | | 1,3-Butylene glycol | 2.00 | 2.00 | 2.00 | 2.00 | 2.00 | 2.00 |
| 24 | | Dipropylene glycol | 6.00 | 6.00 | 6.00 | 6.00 | 6.00 | 6.00 |
| 25 | | Phenoxyethanol | 0.50 | 0.50 | 0.50 | 0.50 | 0.50 | 0.50 |
| 26 | | EDTA-2Na | 0.05 | 0.05 | 0.05 | 0.05 | 0.05 | 0.05 |
| 27 | | Purified water | | | Balance | | | |
| | | Component (D)/component (B) | 1.3 | 1.3 | 0.5 | 0.3 | 0.1 | 2.3 |
| | | Component (D1)/component (B1) | 1.3 | 1.3 | 0.5 | 0.3 | 0.1 | 2.3 |
| | | Component (D2)/component (B1) | | | | | | |
| | | Component (D1)/component (B2) | | | | | | |
| | | Component (D2)/component (B2) | — | — | — | — | — | — |
| | | Viscosity at 25° C. (mPa · s) | 10 | 9 | 8 | 8 | 6 | 18 |
| Evaluation I | | Dispersibility of brilliant powder | A | A | B | B | C | A |
| | | Redispersibility of brilliant powder | A | A | B | C | C | A |
| Evaluation II | Pearlescence | Immediately after filling | A | A | A | A | B | A |
| | | After preservation test | A | A | A | A | B | A |
| | Dispensability | Immediately after filling | A | A | A | A | A | B |
| | | After preservation test | A | A | A | A | A | B |

TABLE 2

| | | | Example | | | | | | |
|---|---|---|---|---|---|---|---|---|---|
| | | | 7 | 8 | 9 | 10 | 11 | 12 | 13 |
| 1 | (A) | Na polyaspartate | 1.00 | 1.00 | 1.00 | 1.00 | 1.00 | 1.00 | 1.00 |
| 2 | | Synthesized smectite | 0.10 | 0.10 | 0.10 | 0.10 | 0.10 | 0.10 | 0.10 |
| 3 | (B) | Aluminum powder | 0.50 | 10.00 | 0.50 | 4.00 | 4.00 | 4.00 | 4.00 |
| 4 | | Titanium oxide-coated glass powder | — | — | — | — | — | — | — |
| 5 | | Brilliant powder*1 | — | — | — | — | — | — | — |
| 6 | (C) | PVP | 2.00 | 2.00 | 2.00 | 2.00 | 2.00 | 2.00 | 2.00 |
| 7 | | PVA | — | — | — | — | — | — | — |
| 8 | | VP/VA copolymer | — | — | — | — | — | — | — |
| 9 | | Alkyl acrylate copolymer*1 | — | — | — | — | — | — | — |
| 10 | (D) | Red iron oxide | 5.00 | 5.00 | 0.30 | — | — | — | — |
| 11 | | Black iron oxide | — | — | — | 5.00 | — | — | — |
| 12 | | Yellow iron oxide | — | — | — | — | 5.00 | — | — |
| 13 | | Titanium dioxide | — | — | — | — | — | 5.00 | — |
| 14 | | Titanium black | — | — | — | — | — | — | 5.00 |
| 15 | | Prussian blue | — | — | — | — | — | — | — |
| 16 | | Carbon black | 3.50 | 3.50 | 3.50 | 3.50 | 3.50 | 3.50 | 3.50 |
| 17 | | Polymer emulsion-1 | 10.00 | 10.00 | 10.00 | 10.00 | 10.00 | 10.00 | 10.00 |
| 18 | | Polymer emulsion-2 | — | — | — | — | — | — | — |
| 19 | | Polymer emulsion-3 | — | — | — | — | — | — | — |
| 20 | | Polyoxyethylene alkyl ether | 1.00 | 1.00 | 1.00 | 1.00 | 1.00 | 1.00 | 1.00 |
| 21 | | Polyoxyethylene glycerin fatty acid ester | 1.00 | 1.00 | 1.00 | 1.00 | 1.00 | 1.00 | 1.00 |
| 22 | | Aminomethyl propanol | 0.10 | 0.10 | 0.10 | 0.10 | 0.10 | 0.10 | 0.10 |
| 23 | | 1,3-Butylene glycol | 2.00 | 2.00 | 2.00 | 2.00 | 2.00 | 2.00 | 2.00 |
| 24 | | Dipropylene glycol | 6.00 | 6.00 | 6.00 | 6.00 | 6.00 | 6.00 | 6.00 |
| 25 | | Phenoxyethanol | 0.50 | 0.50 | 0.50 | 0.50 | 0.50 | 0.50 | 0.50 |
| 26 | | EDTA-2Na | 0.05 | 0.05 | 0.05 | 0.05 | 0.05 | 0.05 | 0.05 |
| 27 | | Purified water | | | | Balance | | | |
| | | Component (D)/component (B) | 10.0 | 0.5 | 0.6 | 1.3 | 1.3 | 1.3 | 1.3 |
| | | Component (D1)/component (B1) | 10.0 | 0.5 | 0.6 | 1.3 | 1.3 | 1.3 | 1.3 |
| | | Component (D2)/component (B1) | | | | | | | |
| | | Component (D1)/component (B2) | | | | | | | |
| | | Component (D2)/component (B2) | — | — | — | — | — | — | — |
| | | Viscosity at 25° C. (mPa · s) | 8 | 14 | 8 | 13 | 14 | 13 | 13 |

TABLE 2-continued

|  |  |  | Example | | | | | | |
|---|---|---|---|---|---|---|---|---|---|
|  |  |  | 7 | 8 | 9 | 10 | 11 | 12 | 13 |
| Evaluation I | Dispersibility of brilliant powder | | A | A | B | B | B | B | B |
|  | Redispersibility of brilliant powder | | A | B | B | B | A | B | B |
| Evaluation II | Pearlescence | Immediately after filling | A | A | B | A | A | A | A |
|  |  | After preservation test | A | A | B | A | A | A | A |
|  | Dispensability | Immediately after filling | A | B | A | B | B | B | B |
|  |  | After preservation test | A | B | A | B | B | B | B |

TABLE 3

|  |  |  | Example | | | | | |
|---|---|---|---|---|---|---|---|---|
|  |  |  | 14 | 15 | 16 | 17 | 18 | 19 |
| 1 | (A) | Na polyaspartate | 1.00 | 1.00 | 1.00 | 1.00 | 1.00 | 1.00 |
| 2 |  | Synthesized smectite | 0.10 | 0.10 | 0.10 | 0.10 | 0.10 | 0.10 |
| 3 | (B) | Aluminum powder | 4.00 | 4.00 | 4.00 | 2.00 | — | — |
| 4 |  | Titanium oxide-coated glass powder | — | — | — | — | 4.00 | — |
| 5 |  | Brilliant powder*1 | — | — | — | 2.00 | — | 4.00 |
| 6 | (C) | PVP | 2.00 | 2.00 | 2.00 | 2.00 | 2.00 | 2.00 |
| 7 |  | PVA | — | — | — | — | — | — |
| 8 |  | VP/VA copolymer | — | — | — | — | — | — |
| 9 |  | Alkyl acrylate copolymer*1 | — | — | — | — | — | — |
| 10 | (D) | Red iron oxide | — | 3.50 | 1.00 | 5.00 | 5.00 | 5.00 |
| 11 |  | Black iron oxide | — | — | — | — | — | — |
| 12 |  | Yellow iron oxide | — | — | — | — | — | — |
| 13 |  | Titanium dioxide | — | — | — | — | — | — |
| 14 |  | Titanium black | — | — | — | — | — | — |
| 15 |  | Prussian blue | 10.00 | 1.50 | 4.00 | — | — | — |
| 16 |  | Carbon black | 3.50 | 3.50 | 3.50 | 3.50 | 3.50 | 3.50 |
| 17 |  | Polymer emulsion-1 | 10.00 | 10.00 | 10.00 | 10.00 | 10.00 | 10.00 |
| 18 |  | Polymer emulsion-2 | — | — | — | — | — | — |
| 19 |  | Polymer emulsion-3 | — | — | — | — | — | — |
| 20 |  | Polyoxyethylene alkyl ether | 1.00 | 1.00 | 1.00 | 1.00 | 1.00 | 1.00 |
| 21 |  | Polyoxyethylene glycerin fatty acid ester | 1.00 | 1.00 | 1.00 | 1.00 | 1.00 | 1.00 |
| 22 |  | Aminomethyl propanol | 0.10 | 0.10 | 0.10 | 0.10 | 0.10 | 0.10 |
| 23 |  | 1,3-Butylene glycol | 2.00 | 2.00 | 2.00 | 2.00 | 2.00 | 2.00 |
| 24 |  | Dipropylene glycol | 6.00 | 6.00 | 6.00 | 6.00 | 6.00 | 6.00 |
| 25 |  | Phenoxyethanol | 0.50 | 0.50 | 0.50 | 0.50 | 0.50 | 0.50 |
| 26 |  | EDTA-2Na | 0.05 | 0.05 | 0.05 | 0.05 | 0.05 | 0.05 |
| 27 |  | Purified water | Balance | | | | | |
| Component (D)/component (B) | | | 2.5 | 1.3 | 1.3 | 1.3 | 1.3 | 1.3 |
| Component (D1)/component (B1) | | | — | 0.9 | 0.3 | 2.5 | 1.3 | — |
| Component (D2)/component (B1) | | | | | | | | |
| Component (D1)/component (B2) | | | | | | | | |
| Component (D2)/component (B2) | | | — | — | — | — | — | — |
| Viscosity at 25° C. (mPa · s) | | | 13 | 8 | 8 | 11 | 11 | 11 |
| Evaluation I | Dispersibility of brilliant powder | | B | B | B | A | A | A |
|  | Redispersibility of brilliant powder | | B | B | C | A | B | A |
| Evaluation II | Pearlescence | Immediately after filling | A | A | A | A | A | C |
|  |  | After preservation test | A | A | A | A | A | C |
|  | Dispensability | Immediately after filling | B | A | A | A | B | A |
|  |  | After preservation test | B | A | A | A | B | A |

TABLE 4

|  |  |  | Example 20 | Example 21 | Example 22 | Example 23 | Example 24 |
|---|---|---|---|---|---|---|---|
| 1 | (A) | Na polyaspartate | 1.00 | 1.00 | 1.00 | 1.00 | 1.00 |
| 2 |  | Synthesized smectite | 0.10 | 0.10 | 0.10 | 0.10 | 0.10 |
| 3 | (B) | Aluminum powder | — | — | — | 2.00 | — |
| 4 |  | Titanium oxide-coated glass powder | — | — | — | — | 2.00 |
| 5 |  | Brilliant powder*1 | 4.00 | 4.00 | 1.00 | 2.00 | 2.00 |
| 6 | (C) | PVP | 2.00 | 2.00 | 2.00 | 2.00 | 2.00 |
| 7 |  | PVA | — | — | — | — | — |
| 8 |  | VP/VA copolymer | — | — | — | — | — |
| 9 |  | Alkyl acrylate copolymer*1 | — | — | — | — | — |
| 10 | (D) | Red iron oxide | — | — | — | — | — |
| 11 |  | Black iron oxide | — | — | — | — | — |
| 12 |  | Yellow iron oxide | — | — | — | — | — |
| 13 |  | Titanium dioxide | — | — | — | — | — |
| 14 |  | Titanium black | — | — | — | — | — |
| 15 |  | Prussian blue | 5.00 | 5.00 | 6.00 | 5.00 | 5.00 |
| 16 |  | Carbon black | 3.50 | — | 3.50 | 3.50 | 3.50 |
| 17 |  | Polymer emulsion-1 | 10.00 | 10.00 | 10.00 | 10.00 | 10.00 |
| 18 |  | Polymer emulsion-2 | — | — | — | — | — |
| 19 |  | Polymer emulsion-3 | — | — | — | — | — |
| 20 |  | Polyoxyethylene alkyl ether | 1.00 | 1.00 | 1.00 | 1.00 | 1.00 |
| 21 |  | Polyoxyethylene glycerin fatty acid ester | 1.00 | 1.00 | 1.00 | 1.00 | 1.00 |
| 22 |  | Aminomethyl propanol | 0.10 | 0.10 | 0.10 | 0.10 | 0.10 |
| 23 |  | 1,3-Butylene glycol | 2.00 | 2.00 | 2.00 | 2.00 | 2.00 |
| 24 |  | Dipropylene glycol | 6.00 | 6.00 | 6.00 | 6.00 | 6.00 |
| 25 |  | Phenoxyethanol | 0.50 | 0.50 | 0.50 | 0.50 | 0.50 |
| 26 |  | EDTA-2Na | 0.05 | 0.05 | 0.05 | 0.05 | 0.05 |
| 27 |  | Purified water | Balance | | | | |
| | | Component (D)/component (B) | 1.3 | 1.3 | 6.0 | 1.3 | 1.3 |
| | | Component (D1)/component (B1) | — | — | — | — | — |
| | | Component (D2)/component (B1) | | | | | |
| | | Component (D1)/component (B2) | | | | | |
| | | Component (D2)/component (B2) | 1.3 | 1.3 | 6.0 | 2.5 | 2.5 |
| | | Viscosity at 25 °C. (mPa · s) | 9 | 7 | 9 | 7 | 7 |
| Evaluation I | Dispersibility of brilliant powder | | B | B | B | C | C |
| | Redispersibility of brilliant powder | | B | B | B | C | C |
| Evaluation II | Pearlescence | Immediately after filling | C | C | C | B | C |
| | | After preservation test | C | C | C | B | C |
| | Dispensability | Immediately after filling | A | A | A | A | A |
| | | After preservation test | A | A | A | A | A |

TABLE 5

|  |  |  | Example 25 | Example 26 | Example 27 | Example 28 | Example 29 |
|---|---|---|---|---|---|---|---|
| 1 | (A) | Na polyaspartate | 1.00 | 1.00 | 1.00 | 1.00 | 1.00 |
| 2 |  | Synthesized smectite | 0.10 | 0.10 | 0.10 | 0.10 | 0.10 |
| 3 | (B) | Aluminum powder | 4.00 | 4.00 | 4.00 | 4.00 | 4.00 |
| 4 |  | Titanium oxide-coated glass powder | — | — | — | — | — |
| 5 |  | Brilliant powder*1 | — | — | — | — | — |
| 6 | (C) | PVP | — | — | — | 2.00 | 2.00 |
| 7 |  | PVA | 2.00 | — | — | — | — |
| 8 |  | VP/VA copolymer | — | 2.00 | — | — | — |
| 9 |  | Alkyl acrylate copolymer*1 | — | — | 2.00 | — | — |
| 10 | (D) | Red iron oxide | 5.00 | 5.00 | 5.00 | 5.00 | 5.00 |
| 11 |  | Black iron oxide | — | — | — | — | — |
| 12 |  | Yellow iron oxide | — | — | — | — | — |
| 13 |  | Titanium dioxide | — | — | — | — | — |
| 14 |  | Titanium black | — | — | — | — | — |
| 15 |  | Prussian blue | — | — | — | — | — |

TABLE 5-continued

|  |  | Example | | | | |
|---|---|---|---|---|---|---|
|  |  | 25 | 26 | 27 | 28 | 29 |
| 16 | Carbon black | 3.50 | 3.50 | 3.50 | 3.50 | 3.50 |
| 17 | Polymer emulsion-1 | 10.00 | 10.00 | 10.00 | — | — |
| 18 | Polymer emulsion-2 | — | — | — | 10.00 | — |
| 19 | Polymer emulsion-3 | — | — | — | — | 10.00 |
| 20 | Polyoxyethylene alkyl ether | 1.00 | 1.00 | 1.00 | 1.00 | 1.00 |
| 21 | Polyoxyethylene glycerin fatty acid ester | 1.00 | 1.00 | 1.00 | 1.00 | 1.00 |
| 22 | Aminomethyl propanol | 0.10 | 0.10 | 0.10 | 0.10 | 0.10 |
| 23 | 1,3-Butylene glycol | 2.00 | 2.00 | 2.00 | 2.00 | 2.00 |
| 24 | Dipropylene glycol | 6.00 | 6.00 | 6.00 | 6.00 | 6.00 |
| 25 | Phenoxyethanol | 0.50 | 0.50 | 0.50 | 0.50 | 0.50 |
| 26 | EDTA-2Na | 0.05 | 0.05 | 0.05 | 0.05 | 0.05 |
| 27 | Purified water | Balance | | | | |
|  | Component (D)/component (B) | 1.3 | 1.3 | 1.3 | 1.3 | 1.3 |
|  | Component (D1)/component (B1) | 1.3 | 1.3 | 1.3 | 1.3 | 1.3 |
|  | Component (D2)/component (B1) |  |  |  |  |  |
|  | Component (D1)/component (B2) |  |  |  |  |  |
|  | Component (D2)/component (B2) | — | — | — | — | — |
|  | Viscosity at 25° C. (mPa·s) | 9 | 13 | 10 | 10 | 12 |
| Evaluation I | Dispersibility of brilliant powder | B | B | C | A | A |
|  | Redispersibility of brilliant powder | A | A | B | A | A |
| Evaluation II | Pearlescence Immediately after filling | B | B | C | A | A |
|  | Pearlescence After preservation test | B | B | C | A | A |
|  | Dispensability Immediately after filling | A | B | B | A | A |
|  | Dispensability After preservation test | A | B | B | A | A |

TABLE 6

|  |  |  | Comparative Example | | |
|---|---|---|---|---|---|
|  |  |  | 1 | 2 | 3 |
| 1 | (A) | Na polyaspartate | — | 1.00 | 1.00 |
| 2 |  | Synthesized smectite | 0.10 | 0.10 | 0.10 |
| 3 | (B) | Aluminum powder | 4.00 | 4.00 | 4.00 |
| 4 |  | Titanium oxide-coated glass powder | — | — | — |
| 5 |  | Brilliant powder*1 | — | — | — |
| 6 | (C) | PVP | 2.00 | — | 2.00 |
| 7 |  | PVA | — | — | — |
| 8 |  | VP/VA copolymer | — | — | — |
| 9 |  | Alkyl acrylate copolymer*1 | — | — | — |
| 10 | (D) | Red iron oxide | 5.00 | 5.00 | — |
| 11 |  | Black iron oxide | — | — | — |
| 12 |  | Yellow iron oxide | — | — | — |
| 13 |  | Titanium dioxide | — | — | — |
| 14 |  | Titanium black | — | — | — |
| 15 |  | Prussian blue | — | — | — |
| 16 |  | Carbon black | 3.50 | 3.50 | 3.50 |
| 17 |  | Polymer emulsion-1 | 10.00 | 10.00 | 10.00 |
| 18 |  | Polymer emulsion-2 | — | — | — |
| 19 |  | Polymer emulsion-3 | — | — | — |
| 20 |  | Polyoxyethylene alkyl ether | 1.00 | 1.00 | 1.00 |
| 21 |  | Polyoxyethylene glycerin fatty acid ester | 1.00 | 1.00 | 1.00 |
| 22 |  | Aminomethyl propanol | 0.10 | 0.10 | 0.10 |
| 23 |  | 1,3-Butylene glycol | 2.00 | 2.00 | 2.00 |
| 24 |  | Dipropylene glycol | 6.00 | 6.00 | 6.00 |
| 25 |  | Phenoxyethanol | 0.50 | 0.50 | 0.50 |
| 26 |  | EDTA-2Na | 0.05 | 0.05 | 0.05 |
| 27 |  | Purified water | Balance | | |
|  |  | Component (D)/component (B) | 1.3 | 1.3 | 0 |
|  |  | Component (D1)/component (B1) | 1.3 | 1.3 | 0 |
|  |  | Component (D2)/component (B1) |  |  |  |
|  |  | Component (D1)/component (B2) |  |  |  |
|  |  | Component (D2)/component (B2) | — | — | 0 |
|  |  | Viscosity at 25° C. (mPa·s) | 8 | 7 | 8 |
| Evaluation I |  | Dispersibility of brilliant powder | C | D | D |
|  |  | Redispersibility of brilliant powder | D | B | D |
| Evaluation II | Pearlescence | Immediately after filling | C | D | D |
|  | Pearlescence | After preservation test | C | D | D |
|  | Dispensability | Immediately after filling | B | B | B |
|  | Dispensability | After preservation test | B | B | B |

Example 30: Eyeliner

| Ingredient | Ratio to be blended (% by mass) |
|---|---|
| 1. Purified water | balance |
| 2. Na polyaspartate | 1.00 |
| 3. Synthesized smectite | 0.10 |
| 4. Metal-coated glass powder | 4.00 |
| 5. PVP | 2.00 |
| 6. Red iron oxide | 1.50 |
| 7. Prussian blue | 3.50 |
| 8. Carbon black | 3.50 |
| 9. Polyoxyethylene alkyl ether | 1.00 |
| 10. Polyoxyethylene glycerin fatty acid ester | 1.00 |
| 11. Aminomethyl propanol | 0.10 |
| 12. 1,3-Butylene glycol | 2.00 |
| 13. Dipropylene glycol | 6.00 |
| 14. Phenoxyethanol | 0.50 |

-continued

| Ingredient | Ratio to be blended (% by mass) |
|---|---|
| 15. EDTA-2Na | 0.05 |
| 16. Polymer emulsion-1 described above | 10.00 |

Production Method

The ingredients 1 to 16 were dissolved and uniformly stirred and mixed to obtain a water-based liquid cosmetic. This cosmetic was filled in an automatic pen type cosmetic container as shown in FIG. 1 to produce an automatic pen type eyeliner.

Evaluation

The eyeliner obtained was evaluated in the same manner as that described above. The viscosity was 9 mPa·s, the dispersibility of the brilliant powder was "B", the redispersibility of the brilliant powder was "B", the pearlescence was "A" both immediately after filling and after the preservation test, and the dispensability was "A" both immediately after filling and after the preservation test.

Example 31: Eyeliner

| Ingredient | Ratio to be blended (% by mass) |
|---|---|
| 1. Purified water | balance |
| 2. Na polyaspartate | 2.00 |
| 3. Synthesized smectite | 0.10 |
| 4. Aluminum powder | 4.00 |
| 5. PVP | 2.00 |
| 6. Red iron oxide | 5.00 |
| 7. Carbon black | 3.50 |
| 8. Polyoxyethylene alkyl ether | 1.00 |
| 9. Polyoxyethylene glycerin fatty acid ester | 1.00 |
| 10. Aminomethyl propanol | 0.10 |
| 11. Dipropylene glycol | 6.00 |
| 12. Phenoxyethanol | 0.50 |
| 13. EDTA-2Na | 0.05 |
| 14. Polymer emulsion-1 described above | 10.00 |

Production Method

The ingredients 1 to 14 were dissolved and uniformly stirred and mixed to obtain a water-based liquid cosmetic. This cosmetic was filled in an automatic pen type cosmetic container as shown in FIG. 1 to produce an automatic pen type eyeliner.

Evaluation

The eyeliner obtained was evaluated in the same manner as that described above. The viscosity was 14 mPa·s, the dispersibility of the brilliant powder was "A", the redispersibility of the brilliant powder was "A", the pearlescence was "A" both immediately after filling and after the preservation test, and the dispensability was "A" both immediately after filling and after the preservation test.

Example 32: Eyeliner

| Ingredient | Ratio to be blended (% by mass) |
|---|---|
| 1. Purified water | balance |
| 2. Na polyaspartate | 1.00 |
| 3. Synthesized smectite | 0.10 |
| 4. Aluminum powder | 5.00 |

-continued

| Ingredient | Ratio to be blended (% by mass) |
|---|---|
| 5. PVP | 2.00 |
| 6. Red iron oxide | 6.00 |
| 7. Carbon black | 1.50 |
| 8. Polyoxyethylene alkyl ether | 1.00 |
| 9. Polyoxyethylene glycerin fatty acid ester | 1.50 |
| 10. Potassium hydroxide | 0.10 |
| 11. 1,3-Butylene glycol | 8.00 |
| 12. Phenoxyethanol | 0.50 |
| 13. EDTA-2Na | 0.05 |
| 14. Xanthan gum | 0.40 |
| 15. Polymer emulsion-1 described above | 15.00 |

Production Method

The ingredients 1 to 15 were dissolved and uniformly stirred and mixed to obtain a water-based liquid cosmetic. This cosmetic was filled in a cosmetic container to produce a bottle type eyeliner.

Evaluation

The eyeliner obtained was evaluated in the same manner as that described above. The viscosity was 4000 mPa·s, the dispersibility of the brilliant powder was "A", the redispersibility of the brilliant powder was "A", the pearlescence was "A" both immediately after filling and after the preservation test, and the applicability was "A" both, immediately after filling and after the preservation test.

It is to be understood that not all aspects, advantages and features described herein may necessarily be achieved by, or included in, any one particular embodiment. Indeed, having described and illustrated various embodiments herein, it should be apparent that other embodiments may be modified in composition and detail. We claim all modifications and variations coming within the spirits and scope of the subject matter claimed herein.

What is claimed is:

1. A water-based liquid cosmetic comprising:
   sodium polyaspartate;
   at least one powder providing pearlescence selected from the group consisting of a glass powder coated with a metal or a metal oxide, an aluminum powder, and a resin film powder coated with a metal;
   a water-soluble dispersant; and
   at least one inorganic pigment selected from the group consisting of yellow iron oxide, red iron oxide, black iron oxide, titanium dioxide, titanium oxynitride, and Prussian blue,
   wherein the water-soluble dispersant comprises at least one water-soluble polymer selected from the group consisting of polyvinylpyrrolidone, polyvinyl alcohol, and a vinylpyrrolidone/vinyl acetate copolymer,
   wherein a content of the sodium polyaspartate is 0.3 to 5% by mass, a content of the powder providing pearlescence is 0.5 to 10% by mass, a content of the water-soluble dispersant is 0.5 to 5% by mass, and a total content of the inorganic pigment is 0.5 to 10% by mass, based on a total amount of the cosmetic, and
   wherein the water-based liquid cosmetic has a viscosity of 50 mPa·s or less at 25° C.

2. The water-based liquid cosmetic according to claim 1, wherein the content of the sodium polyaspartate is 10 to 200 parts by mass, the content of the water-soluble dispersant is 20 to 400 parts by mass, and the content of the inorganic pigment is 12.5 to 1000 parts by mass, per 100 parts by mass of the powder providing pearlescence.

3. The water-based liquid cosmetic according to claim 1, wherein:
  the powder providing pearlescence comprises at least one selected from the group consisting of a glass powder coated with a metal or a metal oxide, and an aluminum powder, and
  the inorganic pigment comprises 12.5 to 1000 parts by mass of at least one selected from the group consisting of yellow iron oxide, red iron oxide, black iron oxide, titanium dioxide, and titanium oxynitride, per 100 parts by mass of a total of the powder providing pearlescence.

4. The water-based liquid cosmetic according to claim 1, wherein:
  the powder providing pearlescence comprises a resin film powder coated with a metal, and
  the inorganic pigment comprises 100 to 600 parts by mass of the Prussian blue, per 100 parts by mass of a total of the resin film powder coated with a metal.

5. The water-based liquid cosmetic according to claim 1, wherein the water-based liquid cosmetic has a viscosity of 20 mPa·s or less at 25° C.

6. The water-based liquid cosmetic according to claim 1, wherein a ratio of the content of the sodium polyaspartate to the content of the water-soluble dispersant is 0.06 to 10.

7. The water-based liquid cosmetic according to claim 1, further comprising a film-forming polymer emulsion.

8. The water-based liquid cosmetic according to claim 7, wherein a content of the film-forming polymer emulsion is 5 to 20% by mass as a solid content based on the total amount of the cosmetic.

9. The water-based liquid cosmetic according to claim 1, further comprising carbon black.

10. The water-based liquid cosmetic according to claim 1, wherein a total of the powder providing pearlescence and the water-soluble dispersant is 0.5 to 20% by mass based on the total amount of the cosmetic.

11. A pen type cosmetic product comprising:
  the water-based liquid cosmetic according to claim 1;
  a cosmetic storing part accommodating the water-based liquid cosmetic; and
  an applicator joined to the cosmetic storing part and comprising a brush, a felt tip, or an urethane tip.

12. The pen type cosmetic product according to claim 11, wherein the pen type cosmetic product is an automatic pen type cosmetic product.

13. The pen type cosmetic product according to claim 12, wherein the pen type cosmetic product is an eyeliner.

* * * * *